United States Patent
Clement et al.

[11] Patent Number: 5,983,900
[45] Date of Patent: Nov. 16, 1999

[54] WRINKLE REMOVAL

[76] Inventors: Robert Marc Clement, 11, Plas Road, Pontardwe, Swansea SA8 3HD, United Kingdom; Michael Noel Kiernan, 89, Heol Eddwch, Seven Sisters, Neath SA10 9AW, United Kingdom

[21] Appl. No.: 08/919,472

[22] Filed: Aug. 28, 1997

[51] Int. Cl.⁶ .................................................. A61B 19/00
[52] U.S. Cl. .............................. 128/898; 607/88; 607/89; 609/2; 609/9
[58] Field of Search ..................... 128/898, 897; 607/88, 89; 606/9, 2

[56] References Cited

U.S. PATENT DOCUMENTS

| | | | |
|---|---|---|---|
| 5,439,954 | 8/1995 | Bush | 424/59 |
| 5,492,894 | 2/1996 | Bascom et al. | 514/18 |
| 5,620,478 | 4/1997 | Eckhouse | 607/88 |
| 5,624,435 | 4/1997 | Furumoto et al. | 606/10 |
| 5,626,631 | 5/1997 | Eckhouse | 607/88 |
| 5,720,772 | 2/1998 | Eckhouse | 607/88 |
| 5,749,868 | 5/1998 | Furumoto | 606/9 |
| 5,755,751 | 5/1998 | Eckhouse | 607/88 |

*Primary Examiner*—Mickey Yu
*Assistant Examiner*—Dinh X. Nguyen
*Attorney, Agent, or Firm*—David P. Gordon; David S. Jacobson; Thomas A. Gallagher

[57] ABSTRACT

Wrinkles are cosmetically removed from a superficial area of mammalian skin tissue having an epidermal layer, a basal layer, and a dermal layer, by irradiating the dermal layer through the basal layer, the irradiation being selected to be absorbed by a chromophore in the dermal layer such that collagen present in the dermal layer is heated, while the basal layer remains intact so as to substantially inhibit contact of the dermal layer with ambient air.

9 Claims, 1 Drawing Sheet

WRINKLE REMOVAL

BACKGROUND TO THE INVENTION

The present invention relates to a method of removing wrinkles from a superficial area of mammalian skin tissue.

The application of laser technology in healthcare is well known, and the use of lasers in medical applications has been studied extensively since the early 1960's. In recent years an increasing interest has been shown in cosmetic applications. One such cosmetic application is skin resurfacing and wrinkle removal; in this field lasers can be used as an alternative to surgical facelifts. A $CO_2$ laser, which operates in the infra-red region of the spectrum, is used, the radiation being totally absorbed in a thin layer of surface tissue, primarily because of the wavelength's high rate of absorption in water.

The current approach used to achieve $CO_2$ laser based skin resurfacing and wrinkle removal involves a two stage process, as follows:

Stage 1—Skin Resurfacing: The purpose of the first stage is to remove a thin layer of tissue from a superficial area of mammalian skin tissue. To achieve this, the skin is irradiated by the laser which, as mentioned above, deposits its energy in a thin layer at the surface (approx 30 $\mu$m in thickness). The application of the laser radiation to the tissue is by computer controlled scanner designed to ensure that one pass of the radiation removes one "layer" of tissue only. In this way, damage is limited to the epidermis only. This process quickly ablates the surface layer removing the surface skin and with it any skin blemishes. The process is straightforward and does not demand a great deal of operator skill. The surface skin immediately starts to replace itself and this allows the skin to return to normal in about 3 to 5 days.

Stage 2—Wrinkle Removal: After the skin surface has been resurfaced, the operator will, typically, apply further "passes" of the laser, thereby removing further layers of mammalian skin tissue, each layer being of the order of 30 $\mu$m thick. Typically, around three or four further passes will complete the wrinkle removal procedure. This treatment therefore produces a controlled second degree burn. The skin barrier to the outside world is removed and therefore, there is a danger of infection.

The required effect is two fold:

(a) the laser induces denaturing of the collagen in the dermis, and the formation of cross links, which results in a tightening effect stretching the skin, reducing or removing the wrinkles (it is thought that the thermal threshold for this effect is a temperature of 70° C.); and (b) the changes to the dermis induce the generation of new collagen which develops using the matrix created by the denatured collagen as a foundation.

The skin-resurfacing and wrinkle removal procedure outlined above is considered by many experts in the field as a significant improvement over previously used surgical methods. The procedure uses the laser's ability to deliver high energy density at the surface of tissue and hence ablate the surface tissue in a well controlled manner. Continuing to remove the tissue, layer by layer is designed to damage the collagen and hence induce wrinkle removal. This second stage of the procedure is primitive; the skin weeps, scabs form and redness of the skin appears for many weeks.

OBJECT OF THE INVENTION

It is therefore the primary object of the present invention to provide a method of removing wrinkles from a superficial area of mammalian skin tissue without causing secondary burns and other problems associated with traditional wrinkle removal.

SUMMARY OF THE INVENTION

If the target for the laser has an appropriate chromophore (a substance that absorbs a specific wavelength and transmits or scatters at other wavelengths) then the laser can be used to modify that target selectively within an inhomogeneous volume of tissue. Occasionally, the desired target does not have a suitable chromophore of its own but exists in close proximity to another material which has such a chromophore which can be selectively targeted. Such interaction is called secondary selective interaction.

The present invention provides a method of removing wrinkles from a superficial area of mammalian skin tissue. The dermal layer of the tissue is irradiated through the basal layer by radiation selected to be absorbed by a chromophore in the dermal layer such that collagen present in the dermal layer is heated, while the basal layer remains intact so as to substantially inhibit contact of the dermal layer with ambient air.

The irradiation of the dermal layer in the method according to the invention is therefore such as to shrink the skin tissue without damage to the dermis (in other words, without causing second degree burns) because the barrier provided by the basal layer remains intact. The method according to the invention is non-invasive and can readily be performed by non-medical personnel.

DESCRIPTION OF PREFERRED EMBODIMENTS

The irradiation may be by means of a source of visible or infra-red radiation (suitably filtered to remove deleterious ultra-violet radiation if necessary). The radiation may be incoherent or, more preferably, coherent (that is from a laser source). Such a laser source may be, for example, a dye laser, a ruby laser, or a semi-conductor laser. If a dye laser is used, its wavelength is preferably such that it is absorbed by oxyhemoglobin (as naturally occurring chromophore present in blood vessels in the dermis). Alternatively, the superficial area may be treated with an artificial chromophore which is absorbed into the dermal layer. Such an artificial chromophore may be applied to the epidermal layer in the form of a liposome-containing topical formulation. The chromophore may then permeate through the basal layer for delivery to the dermal layer.

When a laser is used, it may be arranged to scan the superficial area and/or to irradiate the dermal layer in pulses. When the laser is in pulsed mode, the pulses typically have duration of 10 $\mu$sec to 10 msec (more preferably 100 $\mu$sec to 2 msec).

It is sometimes desirable to remove part of the epidermis prior to irradiating the dermal layer according to the invention. Such epidermis removal (known as skin resurfacing) may be effected mechanically (for example by abrasion), or by means of laser radiation. When laser radiation is used for this purpose, it is typically a scanner controlled $CO_2$ laser source.

DETAILED DESCRIPTION OF THE DRAWINGS

Figure 1:
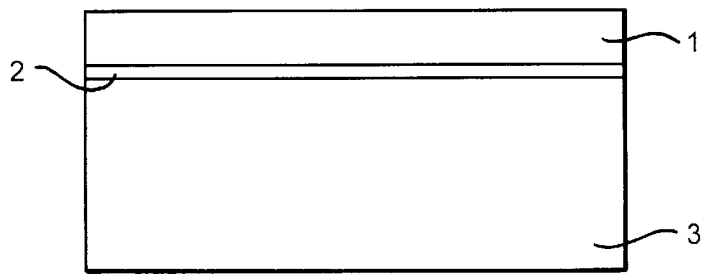
FIG. 1 is a schematic representation of the three outermost layers of mammalian skin tissue.

Referring to FIG. 1, the basic skin structure of mammalian skin tissue comprises three layers, the outermost epidermis 1 which is adjacent to the basal layer 2 and then the dermis 3.

Figure 2:
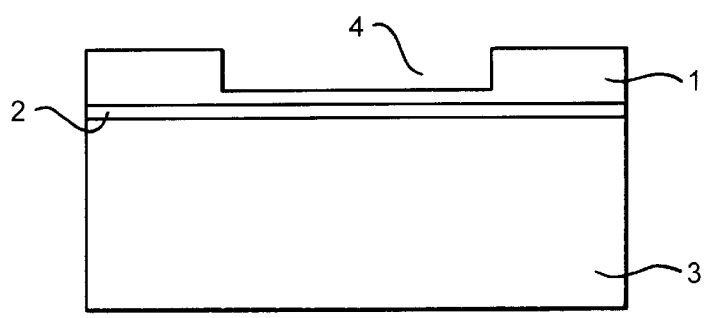
FIG. 2 is a schematic representation of partial removal of the epidermis (skin resurfacing), which is an optional step according to the invention.

Referring to FIG. 2, partial removal of an area 4 of epidermis 1 by means of $CO_2$, laser radiation is known as skin resurfacing. This stage represents the first step of a prior art method but is an optional step according to the invention. Both the basal layer 2 and the dermis 3 are unaffected by the laser radiation.

Figure 3:
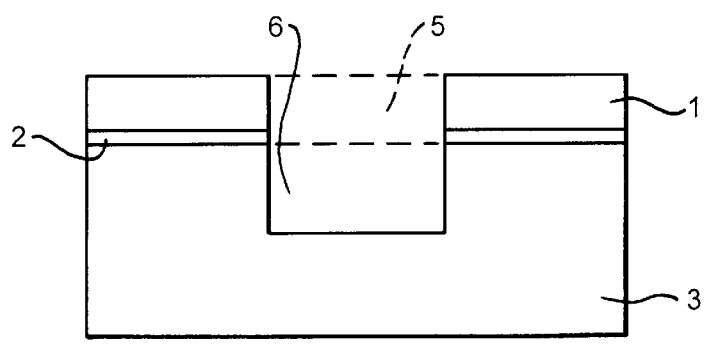
FIG. 3 is a schematic illustration of the result of a prior art method of wrinkle removal, which is surgical because it involves full removal of the epidermis in a selected area and therefore exposure of the dermis and consequent second degree burning.

As shown in FIG. 3, prior art method of wrinkle removal results in complete removal of an area 5 of epidermis 1 and basal layer 2 by repeated exposure to $CO_2$ laser radiation. Partial removal of the dermis 3 also occurs, as represented by 6, leaving the dermis exposed to air. This causes a second degree burn which is slow to heal and a risk of infection.

Figure 4:
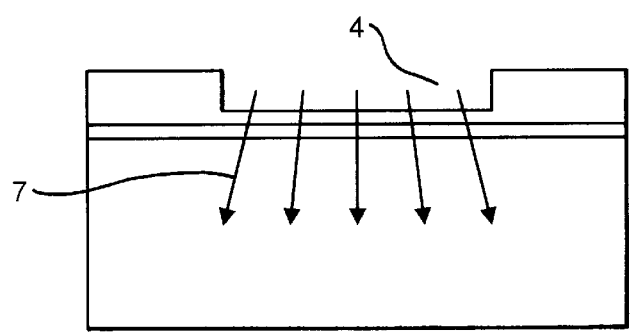
FIG. 4 is a schematic illustration of the result of the method according to the invention, showing that the epidermis is partially intact and the basal layer fully intact.

As shown in FIG. 4, the method of wrinkle removal according to the invention results in partial removal of the epidermis 1 (this is an optional step as described in FIG. 2 above) and the basal layer 2 is left intact, such that the dermis 3 is not exposed to air. Laser radiation 7 is applied to the tissue and selectively absorbed by a chromophore in the dermis 3, heating the collagen and shrinking the skin hence removing the appearance of wrinkles.

We claim:

1. A method of cosmetically removing wrinkles from a superficial area of mammalian skin tissue having, in the order specified, an epidermal layer, a basal layer having blood vessels with blood therein, and a dermal layer having blood vessels with blood therein, which method comprises:

irradiating said dermal layer through said basal layer by means of visible or infrared radiation, without coagulating the blood in the blood vessels of said basal layer and without coagulating the blood in the blood vessels of said dermal layer, said irradiation being selected to be absorbed by a chromophore in said dermal layer such that collagen present in said dermal layer is heated to cause said wrinkles to he removed, while said basal layer remains intact so as to substantially inhibit contact between ambient air and said dermal layers.

2. A method according to claim 1, wherein said irradiation is from a coherent radiation source.

3. A method according to claim 2, wherein said source comprises a ruby laser arranged to target the dermis.

4. A method according to claim 2, wherein said source comprises a dye laser of wavelength selected to target oxyhemoglobin present in blood vessels in said dermal layer.

5. A method according to claim 2, wherein said source comprises a laser selected from one of a dye laser, a ruby laser, and a semiconductor laser which scans said area of mammalian skin tissue.

6. A method according to claim 5, wherein said laser comprising said source is pulsed.

7. A method according to claim 6, wherein said pulsed laser has pulses of duration 10 $\mu$sec to 10 msec.

8. A method according to claim 1, in which said superficial area of mammalian skin tissue is treated with an artificial chromophore which is absorbed into said dermal layer.

9. A method according to claim 8, wherein said artificial chromophore is applied to the epidermal layer in the form of a liposome-containing topical formulation.

* * * * *

UNITED STATES PATENT AND TRADEMARK OFFICE
CERTIFICATE OF CORRECTION

PATENT NO. : 5,983,900
DATED : November 16, 1999
INVENTOR(S) : Robert Marc Clement and Michael Noel Kiernan It is certified that error appears in the above-indentified patent and that said Letters Patent is hereby corrected as shown below:

On title page,

Insert item (30)   Foreign Application Priority Data
August 29, 1996, (GB) United Kingdom, 9618051.1

Signed and Sealed this

Third Day of April, 2001

Attest:

NICHOLAS P. GODICI

Attesting Officer      Acting Director of the United States Patent and Trademark Office